(12) United States Patent
Ohshima et al.

(10) Patent No.: US 6,495,569 B1
(45) Date of Patent: Dec. 17, 2002

(54) IMIDAZOLIDINE COMPOUNDS

(75) Inventors: Etsuo Ohshima, Nagareyama; Hiroki Sone, Shizuoka; Osamu Kotera, Shizuoka; Rie Komatsu, Shizuoka, all of (JP); Gregory J. LaRosa, W. Roxbury; Jay R. Luly, Wellesley, both of MA (US)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/838,657

(22) Filed: Apr. 19, 2001

(51) Int. Cl.$^7$ ............... A61K 31/4164; A61K 31/454; C07D 233/26; C07D 401/12
(52) U.S. Cl. ............... 514/319; 514/326; 514/400; 546/205; 546/210; 548/300.1; 548/314.7
(58) Field of Search ............... 546/205, 210; 514/319, 326, 400; 548/300.1, 314.7

(56) References Cited

U.S. PATENT DOCUMENTS 2,883,368 A * 4/1959 Middleton ............... 508/255

FOREIGN PATENT DOCUMENTS

WO          WO 00/72845 A1      12/2000

OTHER PUBLICATIONS

Foye, W.O., *Principles of Medicinal Chemistry*, 3rd. ed., Philadelphia, Lea & Febiger, pp. 416–425 (1989).

Sasho, S. et al., "Synthesis of 2–Imidazolidinylidenepropanedinitrile Derivatives as Stimulators of Gastrointestinal Motility," *J. Med. Chem.*, 36:572–579 (1993).

* cited by examiner

*Primary Examiner*—Laura L. Stockton
(74) *Attorney, Agent, or Firm*—Hamilton, Brook, Smith & Reynolds, P.C.

(57) ABSTRACT

Disclosed are novel compounds and a method of treating inflammatory diseases. The method comprises administering to an individual in need an effective amount of an imidazolidine compound represented by Structural Formula (I):

(I)

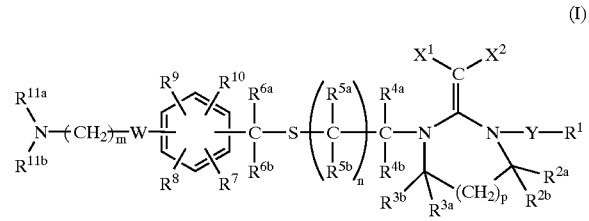

and physiologically or pharmaceutically acceptable salts thereof.

21 Claims, 3 Drawing Sheets

(II)

↓ Step 1-1

(III)

↓ Step 1-2

(IV)

IMIDAZOLIDINE COMPOUNDS

BACKGROUND OF THE INVENTION

Chemokines constitute a family of small cytokines that are produced in inflammation and regulate leukocyte recruitment (Baggiolini, M. et al., *Adv. Immnunol.*, 55: 97–179 (1994); Springer, T. A., *Annu. Rev. Physiol.*, 57: 827–872 (1995); and Schall, T. J. and K. B. Bacon, *Curr. Opin. Immunol.*, 6: 865–873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C-X-C chemokines (α-chemokines) in which the first two conserved cysteines are separated by an intervening residue (e.g., IL-8, IP-10, Mig, I-TAC, PF4, ENA-78, GCP-2, GROα, GROβ, GROγ, NAP-2, NAP-4), and the C-C chemokines (β-chemokines), in which the first two conserved cysteines are adjacent residues (e.g., MIP-1α, MIP-1β, RANTES, MCP-1, MCP-2, MCP-3, I-309)(Baggiolini, M. and Dahinden, C. A., *Immunology Today*, 15:127–133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1–3 (MCP-1, MCP-2 and MCP-3), RANTES (Regulated on Activation, Normal T Expressed and Secreted), and the macrophage inflammatory proteins 1αand 1β(MIP-1αand MIP-1β) have been characterized as chemoattractants and activators of monocytes or lymphocytes, but do not appear to be chemoattractants for neutrophils.

Chemokines (e.g., CC- and CXC-chemokines) act through receptors which belong to a superfamily of seven transmembrane spanning G protein-coupled receptors (Murphy, P. M., *Annu. Rev. Immunol.*, 12: 593–633 (1994); Gerard, C. and N. P. Gerard, *Curr. Opin. Immunol.*, 6: 140–145 (1994)). This family of G protein-coupled (serpentine) receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators.

The chemokine receptors can be divided into groups, which include, CC-chemokine receptors 1 through 9 (CCR1–CCR9), which can bind certain CC-chemokines, and CXC-chemokine receptors 1 through 4 (CXCR1–CXCR4), which can bind certain CXC-chemokines. In general, the CC-chemokine receptors occur on several types of leukocytes, and are important for the migration of monocytes, eosinophils, basophils, and T cells (Qin, S. et al., *Eur. J. Immunol.*, 26: 640–647 (1996); Carr, M.W. et al., Proc. Natl. Acad. Sci. USA, 91(9): 3652–3656 (1994); Taub, D. D. et al., *J. Clin. Invest.*, 95(3): 1370–1376 (1995); Neote, K. et al., *Cell*, 72: 415–425 (1993); Gao, J.-L. et al., *J. Exp. Med.*, 177: 1421–1427 (1993); Charo, I. F. et al., *Proc. Natl. Acad. Sci. USA*, 91: 2752–2756 (1994); Myers, S. J. et al., *J. Biol. Chem.*, 270: 5786–5792 (1995); Combadiere, C. et al.,*J. Biol. Chem.*, 270(27): 16491–16494 (1995); Ponath, P. D. et al, *J. Exp. Med.*, 183: 2437–2448 (1996); Daugherty, B. L. et al., *J. Exp. Med.*, 183: 2349–2354 (1996); Power, C. A. et al., *J. Biol. Chem.*, 270: 19495–19500 (1995); Hoogewerf, A. J. et al., *Biochem. Biophys. Res. Commun.*, 218: 337–343 (1996); and Samson, M. et al., *Biochemistry*, 35: 3362–3367 (1996)).

In contrast, the two IL-8 receptors, CXCR1 and CXCR2, are largely restricted to neutrophils and are important for the migration of neutrophils (Baggiolini, M. et al., *Adv. Immunol.*, 55: 97–179 (1994)). The L-8 receptors, CXCR1 (IL-8R1, interleukin-8 receptor type 1; Holmes, W. E. et al., *Science*, 253: 1278–1280 (1991)) and CXCR2 (IL-8R2, interleukin-8 receptor type 2; Murphy, P. M. and H. L. Tiffany, *Science*, 253: 1280–1283 (1991)) both bind IL-8 and appear to recognize the $NH_2$-terminal Glu-Leu-Arg (ELR) motif as an essential binding epitope observed in CXC-chemokines that induce neutrophil chemotaxis (Clark-Lewis, I. et al., *J. Biol. Chem.*, 266: 23128–23134 (1991); Hebert, C. A. et al., *J. Biol. Chem.*, 266: 18989–18994 (1991); and Clark-Lewis, I. et al., *Proc. Natl. Acad. Sci. USA*, 90: 3574–3577 (1993)). The CXCR1 receptor of human neutrophils binds only IL-8 with high affinity, while the CXCR2 receptor binds IL-8 with similar affinity as CXCR1 but also binds other ELR-containing CXC-chemokines (Baggiolini, M. et al., *Adv. Immunol.*, 55: 97–179 (1994)). Both receptors are capable of coupling to the same G protein α-subunits, exhibiting functional. coupling to Gαi2, Gαi 3, Gα14, Gα15, and Gα16 (Wu, et al., *Science*, 261: 101–103 (1993)). Whether these two receptor subtypes play distinct physiologic roles is not clear.

In contrast to granulocytes and monocytes, lymphocyte responses to chemokines are not well understood. Notably, none of the receptors of known specificity appear to be restricted to lymphocytes and the chemokines that recognize these receptors cannot, therefore, account for events such as the selective recruitment of T lymphocytes that is observed in T cell-mediated inflammatory conditions. Moreover, although a number of proteins with significant sequence similarity and similar tissue and leukocyte subpopulation distribution to known chemokine receptors have been identified and cloned, the ligands for these receptors remain undefined. Thus, these proteins are referred to as orphan receptors. The characterization of the ligand(s) of a receptor, is essential to an understanding of the interaction of chemokines with their target cells, the events stimulated by this interaction, including chemotaxis and cellular activation of leukocytes, and the development of therapies based upon modulation of receptor function.

A chemokine receptor that binds the CXC-chemokines IP-10 and Mig has been cloned and characterized (Loetscher, M. et al., *J. Exp. Med.*, 184: 963–969 (1996)). The receptor mediates $Ca^{2+}$ (calcium ion) mobilization and chemotaxis in response to EP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K.E. et al., *J. Exp. Med.,* 187: 2009–2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.,* 101: 746–754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090–1814 (1993); Taub, D. D. et al., *J. Immunol.*, 155: 3877–3888 (1995); Cole, K. E. et al., *J. Exp. Med.*, 187: 2009–2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128–23134 (1991); Hebert, C. A. et al., *J. Biol. Chem.*, 266: 18989–18994 (1991); and Clark-Lewis, I. et al., *Proc. Natl. Acad. Sci.* USA, 90: 3574–3577 (1993)). In addition, both recombinant human Mig and recombinant human IP-10 have been reported to induce calcium flux in tumor infiltrating lymphocytes (TIL) (Liao, F. et al., *J. Exp. Med.*, 182: 1301–1314 (1995)). While IP-10 has been reported to induce chemotaxis of monocytes in vitro (Taub, D. D. et al., *J. Exp. Med.*, 177: 1809–1814 (1993), the receptor responsible has not been identified), human Mig and I-TAC appear highly selective, and do not show such an effect (Liao, F. et al., *J. Exp. Med.*, 182: 1301–1314 (1995); Cole, K. E. et al., *J. Exp. Med.*, 187: 2009–2021(1998)). IP-10 expression is induced in a variety of tissues in inflammatory conditions such as psoriasis, fixed drug eruptions, cutaneous delayed-type hypersensitivity responses, tuberculoid leprosy, and in experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.,* 178: 1057–1065 (1993); Luster, A. D. et al., *J. Exp. Med.* 182: 219–231 (1995); Angiolillo, A. L. et al., *J. Exp. Med.,* 182: 155–162 (1995); Taub, D. D. et al., *J. Immunol.,* 155: 3877–3888 (1995)). The expression patterns of IP-10, Mig and I-TAC are also distinct from that of other CXC chemokines in that expression of each is induced by interferon-gamma (IFNγ), while the expression of IL-8 is down-regulated by IFNγ (Luster, A. D. et al., *Nature,* 315: 672–676 (1985); Farber, J. M., *Proc. Natl. Acad. Sci.* USA, 87: 5238–5242 (1990); Farber, J. M., *Biochem. Biophys. Res. Commun.,* 192 (1): 223–230 (1993), Liao, F. et al., *J. Exp. Med.,* 182: 1301–1314 (1995); Seitz, M. et al., *J. Clin. Invest.,* 87: 463–469 (1991); Galy, A. H. M. and H. Spits, *J. Immunol.,* 147: 3823–3830 (1991); Cole, K. E. et al., *J. Exp. Med.,* 187: 2009–2021 (1998)).

Chemokines are recognized as the long-sought mediators for the recruitment of lymphocytes. Several CC-chemokines were found to elicit lymphocyte chemotaxis (Loetscher, P. et al., *FASEB J,* 8: 1055–1060 (1994)), however, they are also active on granulocytes and monocytes (Uguccioni, M. et al., *Eur. J. Immunol.,* 25: 64–68 (1995); Baggiolini, M. and C. A. Dahinden, *Immunol. Today,* 15: 127–133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes.

Many existing drugs have been developed as antagonists of the receptors for biogenic amines, for example, as antagonists of the dopamine and histamine receptors. However, no antagonists of the receptors for larger proteins such as chemokines and C5a have been successfully developed and marketed. Small molecule antagonists of the interaction between CXC-chemokine receptors and their ligands, including IP-10, Mig and I-TAC, would provide compounds useful for inhibiting harmful inflammatory processes "triggered" by receptor ligand interaction, as well as valuable tools for the investigation of receptor-ligand interactions.

Diaminoethylene derivatives possessing an electron withdrawing group(s) are known as histamine H2 receptor antagonists and as drugs useful for treating peptic ulcers (*Principles of Medicinal Chemistry,* Foye, W. O., Ed. Lea & Febiger, Philadelphia, 1989, 3rd ed.).

SUMMARY OF THE INVENTION

The present invention relates to small organic compounds which modulate chemokine receptor activity and are useful in the treatment (e.g., palliative therapy, curative therapy, prophylactic therapy) of certain diseases and conditions e.g., inflammatory diseases (e.g., psoriasis), autoimmune diseases (e.g., rheumatoid arthritis, multiple sclerosis), graft rejection (e.g., allograft rejection, xenograft rejection), infectious diseases, cancers. It has now been found that a number of small organic molecules are antagonists of chemokine receptor function (e.g., CXCR3), and can inhibit leukocyte activation and/or recruitment. An antagonist of chemokine receptor function is a molecule which can inhibit the binding of one or more chemokines to one or more chemokine receptors on leukocytes and/or other cell types. As a consequence, and by virtue of the fact that antagonists lack chemokine agonist properties, processes and cellular responses mediated by chemokine receptors can be inhibited with these small organic molecules. In one aspect, the invention relates to small organic compounds which are antagonists of CXCR3. Such CXCR3 antagonists can inhibit binding of one or more chemokines (e.g., CXC-chemokines, such as IP-10, Mig and/or I-TAC) to CXCR3.

The invention also relates to a method of modulating (inhibiting or promoting) an inflammatory response in an individual in need of such therapy. The method comprises administering a therapeutically effective amount of a compound (e.g., small organic molecule) which inhibits or promotes mammalian CXCR3 function to an individual in need thereof.

The invention also relates to a method of treating an individual having a disease associated with pathogenic leukocyte recruitment and/or activation, such as the inflammatory and autoimmune diseases discussed herein. The method comprises administering to the individual a therapeutically effective amount of a compound or small organic molecule which is an antagonist of chemokine receptor function. Compounds or small organic molecules which have been identified as antagonists of chemokine receptor function are discussed in detail herein, and can be used for the manufacture of a medicament for treating or preventing a disease associated with pathogenic leukocyte recruitment and/or activation.

The invention further relates to a compound or small organic molecule described herein for use in therapy (including prophylaxis) or diagnosis, and to the use of such a compound or small organic molecule for the manufacture of a medicament for the treatment of a particular disease or condition as described herein (e.g., inflammatory disease, cancer, autoimmune disease, graft rejection, allergic disease).

The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with inflammation and/or pathogenic leukocyte recruitment and/or activation.

DETAILED DESCRIPTION OF THE INVENTION

Figure 1:
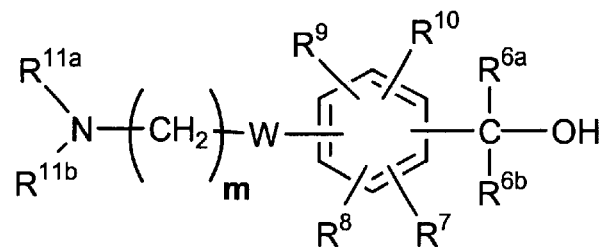
FIG. 1 is schematic diagram showing the preparation of compounds represented by Structural Formula (IV).
Figure 1:
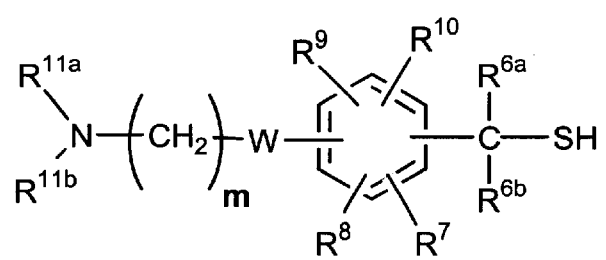
Figure 1:
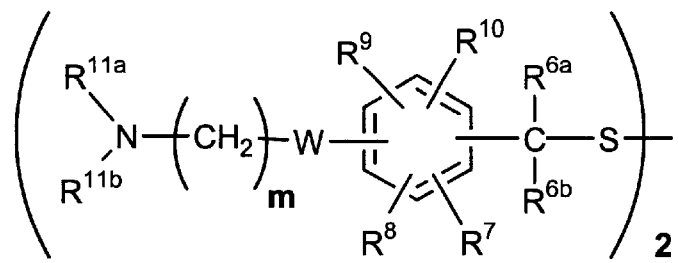

The present invention relates to small organic compounds which modulate chemokine receptor activity and are useful in the prevention or treatment of certain autoimmune and inflammatory diseases and conditions, including, for example, rheumatoid arthritis, psoriasis, graft rejection and multiple sclerosis.

Specifically, the present invention relates to imidazolidine derivatives represented by Structural Formula (I):

(I)

$$\text{structure}$$

and physiologically or pharmaceutically acceptable salts thereof, wherein:

W is
  a bond,
  —O—,
  —S—, or
  —NR$^{12}$—, wherein
    R$^{12}$ represents
      hydrogen,
      substituted or unsubstituted lower alkyl,
      substituted or unsubstituted cycloalkyl,
      substituted or unsubstituted aryl,
      substituted or unsubstituted aralkyl, or
      substituted or unsubstituted heteroarylalkyl;

X$^1$ and X$^2$ are each, independently,
  hydrogen,
  —CN,
  —NO$_2$,
  —SO$_2$R$^{13a}$,
  —SO$_2$NR$^{13a}$R$^{13b}$,
  —C(=O)—R$^{13a}$,
  —C(=O)—OR$^{13a}$, or
  —C(=O)—NR$^{13a}$R$^{13b}$ wherein
    R$^{13a}$ and R$^{13b}$ are each independently,
      hydrogen,
      substituted or unsubstituted lower alkyl,
      substituted or unsubstituted cycloalkyl,
      substituted or unsubstituted aryl, or
      substituted or unsubstituted aralkyl;

Y is
  a bond,
  —(C=O)—, or
  —(CR$^{14a}$R$^{14b}$)—, wherein
    R$^{14a}$ and R$^{14b}$ are each, independently,
      hydrogen,
      substituted or unsubstituted lower alkyl,
      substituted or unsubstituted cycloalkyl,
      substituted or unsubstituted aryl, or
      substituted or unsubstituted aralkyl;

R$^1$ is
  substituted or unsubstituted lower alkyl,
  substituted or unsubstituted cycloalkyl,
  substituted or unsubstituted poly cycloalkyl,
  substituted or unsubstituted lower alkenyl,
  substituted or unsubstituted cycloalkenyl,
  substituted or unsubstituted aryl,
  substituted or unsubstituted heteroaryl,
  substituted or unsubstituted aralkyl, or
  substituted or unsubstituted heteroarylalkyl;

R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each, independently, hydrogen,
substituted or unsubstituted lower alkyl,
substituted or unsubstituted cycloalkyl,
substituted or unsubstituted aryl,
substituted or unsubstituted aralkyl, or
substituted or unsubstituted heteroarylalkyl;
$R^7$, $R^8$, $R^9$ and $R^{10}$ are each, independently,
hydrogen,
hydroxy,
substituted or unsubstituted lower alkyl,
substituted or unsubstituted lower alkoxy,
substituted or unsubstituted lower alkanoyl,
substituted or unsubstituted lower alkanoyloxy
substituted or unsubstituted lower alkoxycarbonyl,
substituted or unsubstituted aryl,
substituted or unsubstituted heteroaryl,
halogen,
—CN,
—NO$_2$,
—COOR$^{15a}$,
—NR$^{15a}$R$^{15b}$, or
—CONR$^{15a}$R$^{15b}$, wherein
$R^{15a}$ and $R^{15b}$ are each, independently,
hydrogen,
substituted or unsubstituted lower alkyl,
substituted or unsubstituted cycloalkyl,
substituted or unsubstituted aryl,
substituted or unsubstituted aralkyl, or
$R^{15a}$ and $R^{15b}$ taken together with the nitrogen atom to which they are bonded form a substituted or unsubstituted heterocyclic group containing at least one nitrogen atom;
$R^{11a}$ and $R^{11b}$ are each, independently,
hydrogen,
substituted or unsubstituted lower alkyl,
substituted or unsubstituted cycloalkyl,
substituted or unsubstituted aryl,
substituted or unsubstituted aralkyl, or
$R^{11a}$ and $R^{11b}$ taken together with the nitrogen atom to which they are bonded form a substituted or unsubstituted heterocyclic group containing at least one nitrogen atom;
n is an integer from 0 to about 4
m is an integer from 0 to about 6; and
p is an integer from 0 to about 2.

Hereinafter, the compound(s) represented by Structural Formula (I) are referred to as Compound(s) (I) or the compound(s) of the present invention. The same applies to the compounds of other formula numbers.

As used herein, the term "alkoxy" refers to —O-alkyl; "alkanoyloxy" refers to —O—C(O)-alkyl; "alkanoyl" refers to —C(O)-alkyl; "alkoxycarbonyl" refers to —C(O)—O—alkyl.

As used herein, the term "lower alkyl" refers to straight-chain or branched alkyl groups having from 1 to about 8 carbon atoms. Lower alkyl groups and the lower alkyl moiety of the lower alkoxy, the lower alkanoyloxy, the lower alkanoyl, the lower alkoxycarbonyl, non-aromatic heterocycloalkyl and the heteroarylalkyl include, for example, methyl, ethyl, propyl, isopropyl, butyl, isobutyl, sec-butyl, tert-butyl, pentyl, hexyl, heptyl and octyl.

A "cycloalkyl" group is a cyclic alkyl group having from 3 to about 10 carbon atoms, for example, cyclopropyl, cyclobutyl, cyclopentyl, cyclohexyl, cycloheptyl, cyclooctyl, cyclononyl and cyclodecyl.

A "poly cycloalkyl" group is a polycyclic alkyl group having from four to about twelve carbon atoms, for example, bicyclo[3.2.1]octyl, bicyclo[4.3.2]undecyl, adamantyl and noradamantyl.

A "lower alkenyl" group is a straight-chain or branched alkyl group having from 2 to about 8 carbon atoms and one or more carbon-carbon double bonds, for example, vinyl, 1-propenyl, allyl, methacryl, 1-butenyl, crotyl, pentenyl, isoprenyl, hexenyl, heptenyl and octenyl.

A "cycloalkenyl" group is a cyclic alkenyl group having from 4 to about 10 carbon atoms, for example, cyclobutenyl, cyclopentenyl, cyclohexenyl, cycloheptenyl, cyclooctenyl, cyclononenyl and cyclodecenyl.

The term "aryl" refers to carbocyclic aromatic groups, including fused polycyclic aromatic ring systems in which a carbocyclic aromatic ring is fused to one or more other carbocyclic aromatic rings. Aryl groups include, for example, phenyl and napthyl.

The term "aralkyl" refers to an aryl-alkyl group having from about 7 to about 15 carbon atoms, for example, benzyl, phenethyl, benzhydryl, naphthylmethyl and acenaphthenyl.

The term "heteroaryl" refers to aromatic heterocyclic groups, including fused polycyclic aromatic ring systems in which an aromatic heterocyclic ring is fused to one or more other aromatic rings, for example, pyridyl, pyrazinyl, pyrimidinyl, pyridazinyl, quinolinyl, isoquinolinyl, phthalazinyl, quinazolinyl, quinoxalinyl, naphthyridinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, purinyl, phenothiazinyl and phenoxazinyl.

A "non-aromatic heterocyclic" group or a "non-aromatic heterocyclo moiety" of the non-aromatic heterocycloalkyl is a cycloaliphatic group that contains one or more heteroatoms, such as nitrogen, oxygen and sulfur. A non-aromatic hereocyclic group can be unsubstituted or substituted with a suitable substituent. Suitable substituents for a non-aromatic hereocyclic group include those substituents described herein, including fused aromatic or non-aromatic rings. Non-aromatic heterocyclic groups which are suitable for use in the invention include, for example, pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolinyl, indolinyl, benzimidazolin-2-on-1-yl, imidazolin-2-on-1-yl, piperazin-2-on-4-yl, piperazine-2,3-dion-1-yl, piperazine-2,5-dion-1-yl, 1-methylpiperazin-4-yl, 1-(2-hydroxyethyl) piperazin-4-yl, 1-(3-hydroxypropyl)piperazin-4-yl, 1-benzylpiperazin-4-yl, dioxanyl, dioxolanyl, tetrahydropyranyl, succinimido and phthalimido.

A "heterocyclic group containing at least one nitrogen atom" can be an aromatic group or a cycloaliphatic group, and includes fused polycyclic ring systems in which a ring containing at least one nitrogen atom is fused to one or more other rings. Examples of heterocyclic groups which contain at least one nitrogen atom include, pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolinyl, indolinyl, benzimidazolin-2-on-1-yl, imidazolin-2-on-1-yl, piperazin-2-on-4-yl, piperazine-2,3-dion-1-yl, piperazine-2,5-dion-1-yl, 1-methylpiperazin-4-yl, 1-(2-hydroxyethyl)piperazin-4-yl, 1-(3-hydroxypropyl)piperazin-4-yl, 1-benzylpiperazin-4-yl, imidazolidyl, imidazolyl, benzimidazolyl, azabenzimidazolyl, succinimido, phthalimido and the like.

Halogens includes fluorine, chlorine, bromine and iodine atoms.

Suitable substituents on a lower alkyl, cycloalkyl, poly cycloalkyl, lower alkenyl, cycloalkenyl, aryl, aralkyl, heteroaryl, heteroarylalkyl, lower alkoxy, lower alkanoyl, lower alkanoyloxy, lower alkoxycarbonyl or heterocyclic group containing at least one nitrogen atom include, for example, halogen, —CN, —NO$_2$, —CF$_3$, hydroxy, oxo, lower alkyl, cycloalkyl, lower alkoxy, lower alkanoyl, lower alkoxycarbonyl, aryl, aralkyl, heteroaryl, heteroarylalkyl, methylenedioxy, non-aromatic heterocyclo, non-aromatic heterocycloalkyl, —COOR$^{16a}$, —NR$^{16a}$R$^{16b}$ and —CONR$^{16a}$R$^{16b}$. R$^{16a}$ and R$^{16b}$ are each, independently, hydrogen, lower alkyl, cycloalkyl, aryl, or aralkyl; or R$^{16a}$ and R$^{16b}$ taken together with the nitrogen atom to which they are bonded form a heterocyclic group containing at least one nitrogen atom.

When a ring (e.g., a cycloalkyl, poly cycloalkyl, cycloaklenyl, aryl, heteroaryl, heterocycloalkyl) is substituted with one or more other rings, the rings can be fused. For example, when a phenyl ring is substituted with dioxolane the rings can be fused to create a benzodioxolanyl group. The substituted groups described herein can have one or more substituent. Preferably, the substituted groups described herein have one to about four substituents which can be the same or different.

In a preferred embodiment, the compound is represented by Structural Formula (I) wherein: W is a bond or —O—; X$^1$ and X$^2$ are —CN; R$^{2a}$, R$^{2b}$, R$^{3a}$, R$^{3b}$, R$^{4a}$, R$^{4b}$, R$^{5a}$, R$^{5b}$, R$^{6a}$, R$^{6b}$, R$^7$, R$^8$, R$^9$, and R$^{10}$ are hydrogen; p is 0; and n is 1. In a particularly preferred embodiment, W is at the para- or meta-position of a benzene ring from the —CR$^{6a}$R$^{6b}$— group; and R$^1$ is substituted or unsubstituted aryl, substituted or unsubstituted heteroaryl, substituted or unsubstituted aralkyl, or substituted or unsubstituted heteroarylalkyl.

Physiologically or pharmaceutically acceptable salts of Compounds (I) include acceptable acid addition salts, metal salts, ammonium salts, and organic amine addition salts. Pharmaceutically or physiologically acceptable acid addition salts of Compounds (I) include inorganic acid addition salts such as hydrochloride, sulfate, nitrate, phosphate and the like, and organic acid addition salts such as acetate, maleate, fumarate, citrate and the like. Pharmaceutically or physiologically acceptable metal salts include alkali metal salts such as sodium salt and potassium salt, alkaline earth metal salts such as magnesium salt and calcium salt, aluminum salt, zinc salt and the like. Pharmaceutically or physiologically acceptable ammonium salts include ammonium, tetramethylammonium and the like; and pharmaceutically or physiologically acceptable organic amine addition salts include addition salts with morpholine, piperidine and the like.

The compounds described herein can be prepared by the synthetic processes shown in FIGS. 1 to 3, which are described below, or other suitable methods.

FIG. 1 is a schematic diagram showing the preparation of compounds represented by Structural Formula (IV) by Process 1. In FIG. 1, the symbols are as defined above.

Step 1-1

The starting Compound (II) can be prepared using suitable methods, for example the methods disclosed in U.S. Pat. No. 4,767,769, EP172631 and DE2917026, the entire teachings of each of which are incorporated herein by reference.

Compound (III) can be obtained by treating Compound (II) with thiourea in the presence of a suitable acid in water at a temperature between about −100° C. and about room temperature for about 5 minutes to about 48 hours, followed by reaction with a suitable aqueous base at a temperature between about 0° C. and the boiling point of the employed solvent for about 5 minutes to about 48 hours.

Acids suitable for use in the reaction include, for example, hydrochloric acid, sulfuric acid, methanesulfonic acid, and trifluoroacetic acid.

Bases suitable for use in the reaction include, for example, sodium hydroxide, potassium hydroxide, lithium hydroxide, cesium hydroxide, sodium methoxide, potassium ethoxide, sodium carbonate, and potassium carbonate.

Step 1-2

Compound (IV) can be prepared by treating Compound (III) obtained in Step 1-1 with a suitable base in a suitable inert solvent at a temperature between about −50° C. and the boiling point of the employed solvent for about 5 minutes to about 48 hours.

Bases suitable for use in the reaction include, for example, sodium hydroxide, potassium hydroxide, potassium carbonate, sodium carbonate, sodium methoxide, potassium methoxide, and potassium ethoxide.

Inert solvents suitable for use in the reaction include, for example, tetrahydrofuran, dioxane, methanol, ethanol, 2-propanol, 1-butanol, dichloromethane, toluene, and dimethylformamide.

Figure 2:
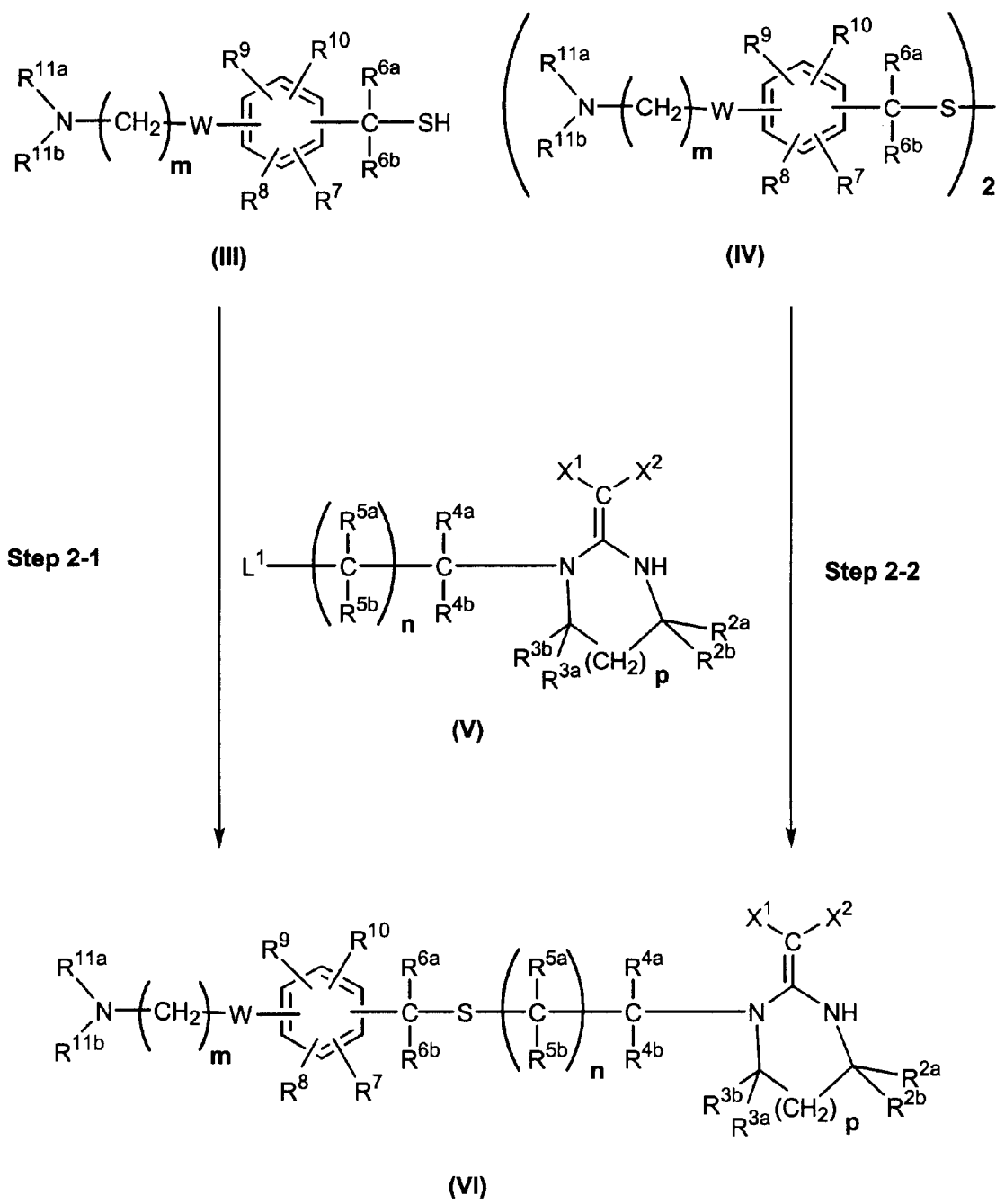
FIG. 2 is schematic diagram showing the preparation of compounds represented by Structural Formula (VI).

FIG. 2 is a schematic diagram showing the preparation of compounds represented by Structural Formula (VI) by Process 2. In FIG. 2, L$^1$ is a suitable leaving group, such as a sulfonate group (e.g., p-toluenesulfonyloxy or methanesulfonyloxy) or a halogen atom (e.g., chlorine, bromine, fluorine or iodine). The other symbols are as described above.

Step 2-1

Compound (V) can be prepared using suitable methods. For example, Compound (V) can be prepared by the methods disclosed in U.S. Pat. No. 5,075,301, JP91-163074, JP92-279581 and JP93-17471 the entire teachings of each of which are incorporated herein by reference. U.S. Pat. No. 5,075,301, JP91-163074, JP92-279581 and JP93-17471 disclose dicyanodiaminoethylene derivatives which inhibit acetylcholinesterases and exhibit gastrointestinal motility enhancing activity.

Compound (VI) can be prepared by reacting Compound (III) obtained in Step 1-1 with Compound (V) in the presence of a suitable base in a suitable inert solvent at a temperature between about −50° C. and the boiling point of the employed solvent for about 5 minutes to about 48 hours.

Bases suitable for use in the reaction include, for example, sodium hydride, potassium hydride, sodium hydroxide, potassium hydroxide, potassium carbonate, sodium carbonate, sodium methoxide, potassium ethoxide, potassium tert-butoxide, butyl lithium, lithium diisopropylamide, triethylamine, tributylamine, N-methylmorpholine, diazabicycloundecene, and diazabicyclononene.

Inert solvents suitable for use in the reaction include, for example, tetrahydrofuran, dioxane, methanol, ethanol, 2-propanol, 1-butanol, dichloromethane, toluene, benzene, hexane, dimethylsulfoxide, and dimethylformamide.

Step 2-2

Compound (VI) can also be obtained by reacting Compound (IV) obtained in Step 1-2 with Compound (V) in the presence of a suitable reducing agent in a suitable inert solvent at a temperature between about −50° C. and the boiling point of the employed solvent for about 5 minutes to about 48 hours.

Reducing agents suitable for use in the reaction include, for example, sodium borohydride, potassium borohydride, diborane, a borane-dimethyl sulfide complex, a borane-tetrahydrofuran complex, a borane-pyridine complex, and a borane-tert-butylamine complex.

Inert solvents suitable for use in the reaction include, for example, tetrahydrofuran, dioxane, methanol, ethanol, 2-propanol, 1-butanol, toluene, benzene, and hexane.

Figure 3:
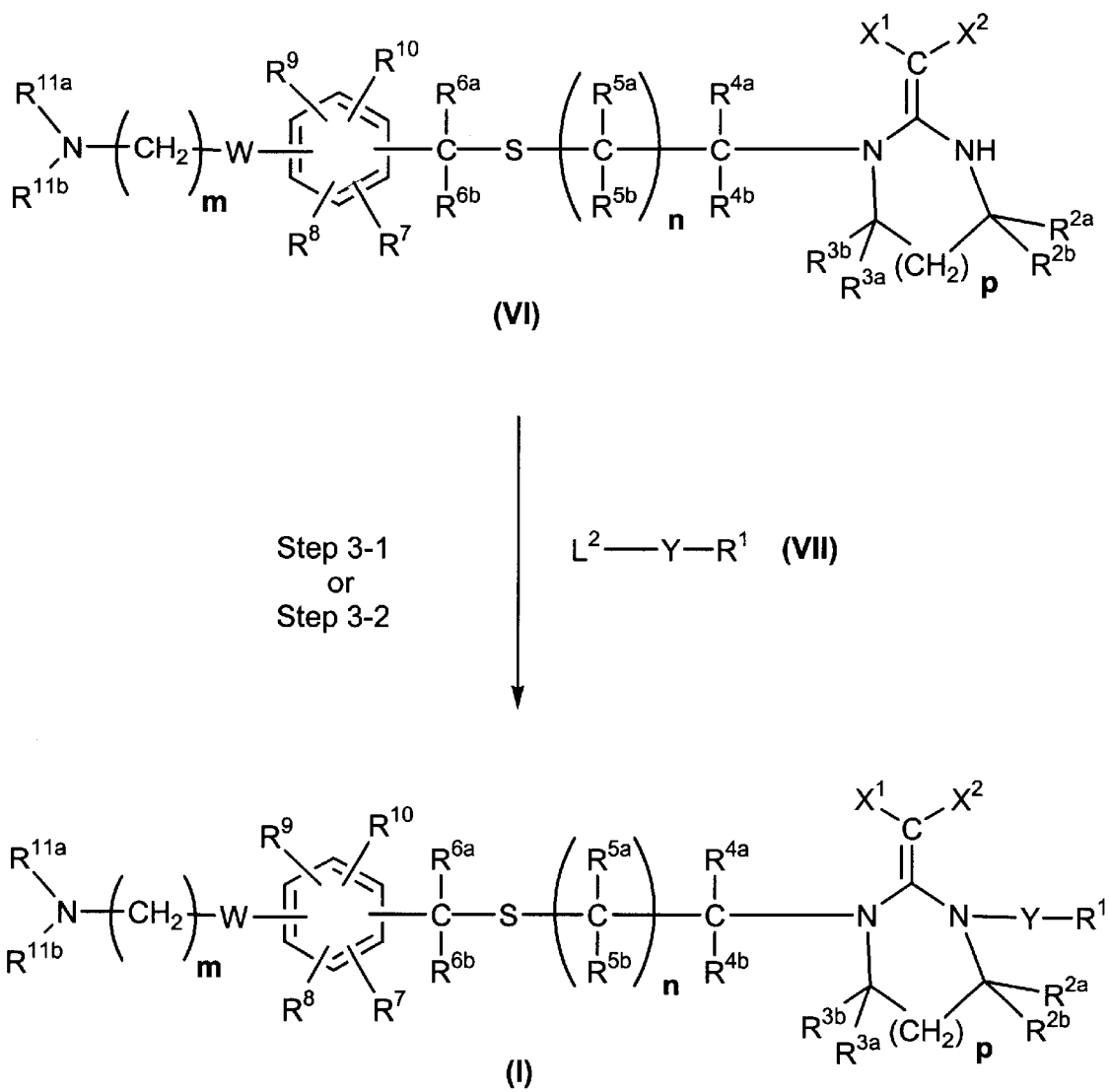
FIG. 3 is schematic diagram showing the preparation of compounds represented by Structural Formula (I).

FIG. 3 is a schematic diagram showing the preparation of compounds represented by Structural Formula (I) by Process 3. In FIG. 3, $L^2$ is a suitable leaving group, such as a hydroxyl group, a sulfonate group (e.g., p-toluenesulfonyloxy or methanesulfonyloxy) or a halogen atom (e.g., chlorine, bromine, fluorine or iodine). The other symbols are as described above.

Step 3-1

Compound (I) can be prepared by reacting Compound (VI) obtained in Step 2-1 or 2-2 with Compound (VII) in the presence of a suitable base in a suitable inert solvent at a temperature between about −100° C. and the boiling point of the employed solvent for about 5 minutes to about 48 hours. If desired, a suitable catalyst can be used.

Bases suitable for use in the reaction include, for example, sodium hydride, potassium hydride, sodium hydroxide, potassium hydroxide, potassium carbonate, sodium carbonate, sodium methoxide, potassium ethoxide, potassium tert-butoxide, butyl lithium, lithium diisopropylamide, triethylamine, tributylamine, N-methylmorpholine, diazabicycloundecene, and diazabicyclononene.

Inert solvents suitable for use in the reaction include, for example, tetrahydrofuran, dioxane, methanol, ethanol, 2-propanol, 1-butanol, dichloromethane, toluene, benzene, hexane, dimethyl sulfoxide, and dimethylformamide.

Catalysts which are suitable for use in the reaction include, for example, 18-crown-6, 15-crown-5, and benzyltrimethylammonium hydroxide. Step 3-2:

Compound (1) can also be prepared by reacting Compound (VI) obtained in Step 2-1 or 2-2 with Compound (VII) in the Mitsunobu reaction conditions (*Advanced Organic Chemistry,* Carey, F. A.; Sundberg, R. J., Ed. Plenum, N.Y., 1990, 3rd ed.). For example, Compound (VI) can be treated with a mixture of Compound (VII), triphenylphosphin, and diethyl azodicarboxylate in a suitable inert solvent under a suitable inert gas at a temperature between about −100° C. and about room temperature for about 5 minutes to about 96 hours.

Inert solvents suitable for use in the reaction include, for example, tetrahydrofuran, dioxane, dichloromethane, toluene, and benzene.

Inert gases suitable for use in the reaction include, for example, argon, helium, and nitrogen.

The intermediates and the desired compounds produced by the processes described herein can be isolated using suitable methods, for example, filtration, extraction, washing, drying, concentration, recrystallization and various kinds of chromatography. The intermediates can also be subjected to subsequent reactions without isolation.

The compounds of the invention can be produced as a salt or as free compounds. The desired salt of a compound of the invention can be prepared by dissolving or suspending the compound in a suitable solvent and adding a suitable acid or base to the solution, thereby forming a salt. When the compound is produced as a salt, it can be purified as such.

Compound (I) and pharmaceutically acceptable salts thereof may be in the form of adducts with water or various solvents, which are also within the scope of the present invention.

The activity of the compounds of the present invention can be assessed using a suitable assay, such as a receptor binding assay, a chemotaxis assays, an extracellular acidification assay or a calcium flux assay (see, for example, Hesselgesser et al., *J. Biol. Chem.* 273(25):15687–15692 (1998) and WO 98/02151). For example, as described herein, small organic molecule antagonists of CXCR3/IP-10 binding have been identified utilizing cells engineered to express recombinant human CXCR3 (CXCR3.L1/2) and which bind $^{125}$I-IP10 and chemotax in response to IP-10, Mig or I-TAC. Specifically, a high through-put receptor binding assay, which monitors $^{125}$I-IP10 binding to CXCR3.L1/2 cell membranes, was used to identify small molecule antagonists which block binding of IP-10, Mig or I-TAC to CXCR3.

The activity of the compounds can also be assessed by monitoring cellular responses induced by active receptor, using suitable cells expressing receptor. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.,* 155: 3877–3888 (1995), regarding assays for release of granule-derived serine esterases; Loetscher et al., *J. Immunol.,* 156: 322–327 (1996), regarding assays for enzyme and granzyme release; Rot, A. et al, *J. Exp. Med.,* 176: 1489–1495 (1992) regarding respiratory burst; Bischoff, S. C. et al, *Eur. J. Immunol,* 23: 761–767 (1993) and Baggliolini, M. and C. A. Dahinden, *Immunology Today,* 15: 127–133 (1994)).

In one embodiment, an antagonist of CXCR3 is identified by monitoring the release of an enzyme upon degranulation or exocytosis by a cell capable of this function. Cells expressing CXCR3 can be maintained in a suitable medium under suitable conditions, and degranulation can be induced. The cells are contacted with an agent to be tested, and enzyme release can be assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.,* 155: 3877–3888 (1995) regarding release of granule-derived serine esterases).

In another embodiment, cells expressing CXCR3 are combined with a ligand of CXCR3 (e.g., IP-10, Mig, I-TAC) or promoter of CXCR3 function, a compound to be tested is added before, after or simultaneous therewith, and degranulation is assessed. Inhibition of ligand- or promoter-induced degranulation is indicative that the compound is an inhibitor of mammalian CXCR3 function (a CXCR3 antagonist).

Therapeutic Applications

The compounds of the present invention are useful in the treatment of certain diseases or conditions (e.g., autoimmune, inflammatory, infectious, cancer). Modulation of mammalian CXCR function according to the present invention, through the inhibition or promotion of at least one function characteristic of a mammalian CXCR protein, provides an effective and selective way of inhibiting or promoting receptor-mediated functions. As CXC-chemokine receptors selectively expressed on activated lymphocytes, responsive to chemokines such as IP-10, Mig or I-TAC whose primary targets are lymphocytes, particularly effector cells such as activated or stimulated T lymphocytes and NK cells, mammalian CXCR3 proteins provide a target for selectively interfering with or promoting lymphocyte function in a mammal, such as a human. Once lymphocytes are recruited to a site, other leukocyte types, such as monocytes, may be recruited by secondary signals. Thus, agents which inhibit or promote CXCR3 function, including inhibitors (antagonists) and/or promoters (agonists), such as the compounds described herein, can be used to modulate leukocyte function (e.g., leukocyte infiltration including recruitment and/or accumulation), particularly of lymphocytes, for therapeutic purposes.

In one aspect, the present invention provides a method of modulating (inhibiting or promoting) an inflammatory response in an individual in need of such therapy, comprising administering an agent which inhibits or promotes mammalian CXCR3 function to an individual in need of such therapy. In one embodiment, a compound which inhibits one or more functions of a mammalian CXCR3 protein (e.g., a human CXCR3) is administered to inhibit (i.e., reduce or prevent) inflammation. For example, the small organic molecules of the present invention, including Compound 1 can be used in the method. As a result, one or more inflammatory processes, such as leukocyte emigration, chemotaxis, exocytosis (e.g., of enzymes) or inflammatory mediator release, can be inhibited. For example, leukocytic infiltration of inflammatory sites (e.g., in a delayed-type hypersensitivity response) can be inhibited according to the present method. The inflammation can be acute or chronic and can be a consequence of an autoimmune disease, allergic reaction, infection (e.g., bacterial, viral, fungal, parasitic) or trauma (e.g., ischemia/reperfusion injury), for example.

In another embodiment, a compound which promotes one or more functions (e.g., receptor agonist) of a mammalian CXCR3 protein (e.g., a human CXCR3) is administered to induce (trigger or enhance) an inflammatory response, such as leukocyte emigration, chemotaxis, exocytosis (e.g., of enzymes) or inflammatory mediator release, resulting in the beneficial stimulation of inflammatory processes. For example, natural killer cells can be recruited to combat viral infections or neoplastic disease.

In another embodiment, the present invention is a method of treating (e.g., palliative therapy, curative therapy, maintenance therapy, prophylactic therapy) an individual having a disease associated with pathogenic leukocyte recruitment and/or activation. The method comprises administering a compound which inhibits mammalian CXCR3 function (e.g., a compound of Structural Formula I or physiologically or pharmaceutically acceptable salt thereof) to an individual in need of such therapy. Where the individual has a relapsing or chronic condition, an effective amount of an a compound which inhibits mammalian CXCR3 function (e.g., a compound of Structural Formula I or physiologically or pharmaceutically acceptable salt thereof) can be administered to treat the condition, and therapy can be continued (maintenance therapy) with the same or different dosing as indicated, to inhibit relapse or renewed onset of symptoms.

The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic and/or prophylactic purposes. In a particularly preferred embodiment, the inflammatory disease or condition is a T cell-mediated disease or condition.

Diseases or conditions, including chronic diseases, of humans or other species which can be treated with inhibitors of CXC chemokine receptor 3 (CXCR3) function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis, juvenile rheumatoid arthritis, polyarthritis, spondyloarthropathy), multiple sclerosis, systemic lupus erythematosus, myasthenia gravis, diabetes, including diabetes mellitus and juvenile onset diabetes, glomerulonephritis and other nephritides, autoimmune thyroiditis, Behcet's disease;

graft rejection (e.g., in transplantation), including allograft rejection, xenograft rejection or graft-versus-host disease;

other diseases or conditions in which undesirable inflammatory responses are to be inhibited can be treated, including, but not limited to, atherosclerosis, restenosis, cytokine-induced toxicity, myositis (including polymyositis, dermatomyositis);

diseases in which angiogenesis or neovascularization plays a role, including neoplastic disease (e.g., tumor formation and growth), retinopathy (e.g., retinopathy of prematurity, diabetic retinopathy), retinal vein occlusion, macular degeneration (e.g., age-related macular degeneration), hemangiomas, arthritis (e.g., rheumatoid arthritis) and psoriasis.

Diseases or conditions of humans or other species which can be treated with a promoter (e.g., an agonist) of CXC chemokine receptor 3 (CXCR3) function, include, but are not limited to:

cancers, particularly those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes. Promoters of CXCR3 function can also have protective effects useful to combat stem cell depletion during cancer chemotherapy (Sarris, A. H. et al., *J. Exp. Med.*, 178: 1127–1132 (1993)).

Modes of Administration

According to the method, one or more compounds can be administered to an individual by an appropriate route, either alone or in combination with another drug. A therapeutically effective amount of an agent (e.g., a small organic molecule which inhibits ligand binding) is administered. A "therapeutically effective amount" of a compound is an amount which is sufficient to achieve a desired therapeutic and/or prophylactic effect, such as an amount which results in the prevention or a decrease in the severity of symptoms associated with an inflammatory disease or condition. For example, an effective amount of an antagonist of CXCR3 function is an amount sufficient to inhibit a (i.e., one or more) function of CXCR3 (e.g., ligand (e.g., IP-10, Mig, I-TAC) bindind, ligand-induced leukocyte migration, ligand-induced integrin activation, ligand-induced transient increases in the concentration of intracellular free calcium $[Ca^2+]_i$ and ligand-induced granule release of proinflammatory mediators).

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, a therapeutically effective amount of the compound can range from about 0.1 mg per day to about 100 mg per day for an adult. Preferably, the dosage ranges from about I mg per day to about 100 mg per day. An antagonist of chemokine receptor function can also be administered in combination with one or more additional therapeutic agents, e.g., theophylline, β-adrenergic bronchdilators, corticosteroids, antihistamines, antiallergic agents, immunosuppressive agents and the like.

The compound of the invention can be administered by any suitable route, including, for example, orally in capsules, suspensions or tablets or by parenteral administration. Parenteral administration can include, for example, intramuscular, intravenous, subcutaneous, intrathecal or intraperitoneal administration. The compound can also be administered orally (e.g., dietary), transdermally, topically, by inhalation (e.g., intrabronchial, intranasal, oral inhalation or intranasal drops) or rectally. Administration can be local or systemic as indicated. The preferred mode of administration can vary depending upon the particular disease or condition to be treated, however, oral or parenteral administration is generally preferred.

The compound can be administered to the individual in conjunction with a physiologically or pharmaceutically acceptable carrier as part of a pharmaceutical composition for treatment or prevention of inflammation, an inflammatory disease or other disease (e.g., an autoimmune disease), as described herein. Formulation of a compound to be administered will vary according to the route of administration selected (e.g., solution, emulsion, capsule). Suitable physiologically or pharmaceutically acceptable carriers may contain inert ingredients which do not interact with the compound. Standard pharmaceutical formulation techniques can be employed, such as those described in Remington's Pharmaceutical Sciences, Mack Publishing Company, Easton, Pa. Suitable physiologically or pharmaceutically acceptable carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker et al., "Controlled Release of Biological Active Agents", John Wiley and Sons, 25 1986).

The compounds of the present invention can also be administered to treat a inflammatory and/or autoimmune diseases or conditions in combination with a variety of other anti-inflammatory and/or immunosuppressive drugs, such as cyclosporin A, rapamycin, steroids (e.g., prednisone, methylpednisolone), azothioprine, methotrexate, or FK506 (tacrolimus). Such combination therapy can result in more efficacious therapy with reduced doses of the anti-inflammatory or immunosuppressive drugs. The ability to reduce the dose of the anti-inflammatory or immunosuppressive drug can greatly benefit the patient as many of these drugs have severe and well-known side effects (Spencer, C. M. et al., *Drugs*, 54(6):925–975 (1997); *Physicians Desk Reference*, $53^{rd}$ Edition, Medical Economics Co., pp. 2081–2082 (1999)).

The invention is illustrated by the following Examples and Test Example which are not intended to be limiting in any way.

Exemplification

EXAMPLE 1

1-{2-(3-Piperidinomethylbenzylthio)ethyl}-3-(1-naphthylmethyl)-2-imidazolidinylidenepropanedinitrile (Compound 1)

In anhydrous tetrahydrofuran (THF) (75 ml) were dissolved Compound (I) (100 mg) obtained in Reference Example 1, 1-naphthalenemethanol (62 mg), and triphenylphosphine (113 mg). To the solution was added diethyl azodicarboxylate (99 mg), followed by stirring at room temperature for 12 hours. The solvent was evaporated under reduced pressure, and the residue was purified by flash silica gel column chromatography (chloroform : methanol =100:1 to 20:1). The resulting product was recrystallized from ethanol to give 68 mg (49%) of Compound 1 as colorless crystals.

Melting point: 150–155° C.

$^1$H NMR (270 MHz, CDCl$_3$) δ: 7.9–7.2 (11H, m), 5.21 (2H, s), 3.80 (2H, s), 3.71 (2H, t, J=6.8 Hz), 3.5–3.2 (6H, m), 2.80 (2H, t, J=6.8 Hz), 2.39 (4H, brs), 1.57 (4H, brs), 1.42 (2H, brs)

Elemental analysis: $C_{32}H_{35}N_5S_10.4H_2O$

| | |
|---|---|
| Found (%) | C: 72.55, H: 6.76, N: 13.37 |
| Calculated (%) | C: 72.67, H: 6.82, N: 13.24 |

EXAMPLE 2

1- {2-(4-Piperidinomethylbenzylthio)ethyl}-3-(1-naphthylmethyl)-2-imidazolidinylidenepropanedinitrile (Compound 2)

Compound 2 (302 mg, 58%) was obtained as colorless crystals by following the procedure of Example 1, but replacing Compound (I) with Compound (IV) (382 mg) obtained in Reference Example 2.

Melting point: 117–119° C.

$^1$H NMR (270 MHz, CDCl$_3$) δ: 8.0–7.3 (11H, m), 5.21 (2H, s), 3.78 (2H, s), 3.71 (2H, t, J=6.6 Hz), 3.5–3.2 (6H, m), 2.79 (2H, t, J=6.6 Hz), 2.34 (4H, brs), 1.55 (4H, brs), 1.43 (2H, brs)

Elemental analysis: $C_{32}H_{32}N_5S_1$

| Found (%) | C: 73.67, H: 6.76, N: 13.42 |
|---|---|
| Calculated (%) | C: 73.44, H: 6.78, N: 13.26 |

EXAMPLE 3

1-{2-(3-Piperidinomethylbenzylthio)ethyl}-3-(2,3-dimethylbenzyl)-2-imidazolidinylidenepropanedinitrile (Compound 3)

A reaction was conducted by using Compound (I) (285 mg) obtained in Reference Example 1 and 2,3-dimethylbenzyl alcohol (285 mg) as described in Example 1. The resulting product was recrystallized in acetone in the form of an oxalate to give Compound 3 (282 mg, 58%) as colorless crystals.

Melting point: 169–171° C.

$^1$H NMR (270 MHz, CDCl$_3$) δ: 7.9–7.3 (7H, m), 4.77 (2H, s), 3.79 (2H, s), 3.70 (2H, t, J=6.8 Hz), 3.5–3.2 (6H, m), 2.80 (2H, t, J=6.8 Hz), 2.38 (4H, brs), 2.30 (3H, s), 2.18 (3H, s), 1.60 (4H, brs), 1.43 (2H, brs)

| Found (%) | C: 65.14, H: 6.68, N: 11.84 |
|---|---|
| Calculated (%) | C: 65.17, H: 6.67, N: 11.88 |

EXAMPLE 4

1-{2-(3-Piperidinomethylbenzylthio)ethyl}-3-(1-acenaphthenyl)-2imidazolidinylidenepropanedinitrile (Compound 4)

Compound 4 was prepared by following the procedure of Example 1, but replacing 1-naphthalenemethanol with 1-acenaphthenol (134 mg). The resulting product was recrystallized in acetone in the form of an oxalate to give Compound 4 (280 mg, 83%) as colorless crystals.

Melting point: 179–181 ° C.

$^1$H NMR (270 MHz, CDCl$_3$) δ: 7.85 (1H, d, J=8.2 Hz), 7.75 (1H, d, J=8.3 Hz), 7.6–7.4 (8H, m), 6.26 (1H, dd, J=7.9 Hz, 3.0 Hz), 4.11 (2H, s), 3.89 (2H, s), 3.8–3.3 (8H, m), 2.95 (4H, brs), 2.76 (2H, t, J=6.9 Hz), 1.67 (4H, brs), 1.48 (2H, brs), Elemental analysis: $C_{38}H_{35}N_5S_1·1.0C_2H_2O_4·0.2H_2O$

| Found (%) | C: 66.85, H: 6.21, N: 10.99 |
|---|---|
| Calculated (%) | C: 67.00, H: 6.01, N: 11.16 |

EXAMPLE 5

1-{2-(3-Piperidinomethylbenzylthio)ethyl}-3-{1-(1-naphthyl)ethyl}-2-imidazolidinylidenepropanedinitrile (Compound 5)

Compound 5 was prepared by following the procedure of Example 1, but replacing 1-naphthalenemethanol with -methyl-1-naphthalenemethanol (162 mg). The resulting product was recrystallized in acetone in the form of an oxalate to give Compound 5 (237 mg, 94%) as colorless crystals.

Melting point: 83–84° C.

$^1$H NMR (270 MHz, DMSO-d$_6$) δ: 8.0–7.9 (3H, m), 7.7–7.5 (4H, m), 7.4–7.3 (4H, m), 6.14 (1H, q, J=6.6 Hz), 4.09 (2H, s), 3.83 (2H, s), 3.6–3.3 (6H, m), 3.29 (4H, brs), 2.7–2.6 (2H, m), 1.75 (3H, d, J=6.6 Hz), 1.66 (4H, brs), 1.48 (2H, brs)

Elemental analysis: $C_{33}H_{37}N_5S_1·1.0C_2H_2O_4·0.3H_2O$

| Found (%) | C: 66.72, H: 6.42, N: 11.00 |
|---|---|
| Calculated (%) | C: 66.60, H: 6.32, N: 11.09 |

EXAMPLE 6

1-{2-(3-Piperidinomethylbenzylthio)ethyl}-3-(2,3-methylenedioxybenzyl)-2-imidazolidinylidenepropanedinitrile (Compound 6)

Compound 6 was prepared by following the procedure of Example 1, but replacing 1-naphthalenemethanol with 3-hydroxymethylbenzodioxol (236 mg). The resulting product was recrystallized in acetone in the form of an oxalate to give Compound 6 (184 mg, 72%) as colorless crystals.

Melting point: 136–141° C.

$^1$H NMR (270 MHz, DMSO-d$_6$) δ: 7.4–7.3 (4H, m), 6.9–6.8 (3H, s), 6.02 (2H, s), 4.67 (2H, s), 4.08 (2H, s), 3.86 (2H, s), 3.7–3.5 (6H, m), 2.90 (4H, brs), 2.9–2.7 (2H, m), 1.65 (4H, brs), 1.48 (2H, brs)

Elemental analysis: $C_{29}H_{33}N_5O_2S_1·1.0C_2H_2O_4$

| Found (%) | C: 61.35, H: 5.89, N: 11.55 |
|---|---|
| Calculated (%) | C: 61.47, H: 5.82, N: 11.56 |

EXAMPLE 7

1-{2-(3-Piperidinomethylbenzylthio)ethyl}-3-(1-naphthoyl)-2-imidazolidinylidenepropanedinitrile (Compound 7)

In THF (50 ml) was dissolved Compound (I) (180 mg) obtained in Reference Example 1, potassium tert-butoxide (79 mg) was added thereto at 0° C., followed by stirring for 30 minutes. To the mixture was dropwise added 1-naphthoyl chloride (134 mg), followed by further stirring for 10 minutes. An aqueous solution of sodium bicarbonate was added thereto, and the reaction mixture was extracted with chloroform. The solvent was evaporated under reduced pressure, and the residue was purified by silica gel column chromatography (chloroform: methanol=100:1 to 20:1) to give Compound 7 (156 mg, 62%) as a colorless oily substance.

$^1$H NMR (270 MHz, CDCl$_3$) δ: 8.17 (1H, d, J=8.7 Hz), 7.99 (1H, d, J=8.4 Hz), 7.90 (1H, d, J=6.9 Hz), 7.7–7.4 (4H, m), 7.3–7.2 (4H, m), 3.80 (2H, t, J=6.4 Hz), 3.78 (2H, s), 3.7–3.5 (4H, m), 3.47 (2H, s), 2.83 (2H, t, J=6.9 Hz), 2.38 (4H, brs), 1.55 (4H, brs), 1.43 (2H, brs)

EXAMPLE 8

1-{2-(2-Piperidinomethylbenzylthio)ethyl}-3-(1-naphthylmethyl)-2-imidazolidinylidenepropanedinitrile (Compound 8)

Compound 8 was prepared by following the procedure of Example 1, but using Compound (V) (240 mg) obtained in Reference Example 3 and 1-naphthalenemethanol (149 mg). The resulting product was recrystallized in acetone in the form of an oxalate to give Compound 8 (259 mg, 68%) as colorless crystals.

Melting point: 169–173° C.

$^1$H NMR (270 MHz, DMSO-d$_6$) δ: 8.0–7.9 (3H, m), 7.6–7.3 (8H, m), 5.22 (2H, s), 4.14 (2H, s), 4.03 (2H, s), 3.73 (2H, t, J=7.9 Hz), 3.7–3.5 (2H, m), 3.5–3.4 (2H, m), 2.94 (4H, m), 2.81 (2H, t, J=7.4 Hz), 1.66 (4H, brs), 1.49 (2H, brs)

Elemental analysis: $C_{32}H_{35}N_5S_1 \cdot 1.0C_2H_2O_4 \cdot 0.2H_2O$

| | |
|---|---|
| Found (%) | C: 66.45, H: 6.20, N: 11.38 |
| Calculated (%) | C: 66.36, H: 6.13, N: 11.38 |

EXAMPLE 9

1-{2-(3-Piperidinomethylbenzylthio)ethyl}-3-(1,2-diphenylethyl)-2-imidazolidinylidenepropanedinitrile (Compound 9)

Compound 9 was prepared by following the procedure of Example 1, but replacing 1-naphthalenemethanol with 1,1,2-diphenylethanol (210 mg). The resulting product was recrystallized in acetone in the form of an oxalate to give Compound 9 (160 mg, 54%) as colorless crystals.

Melting point: 112–118° C.

$^1$H NMR (270 MHz, CDCl$_3$) δ: 7.4–7.2 (14H, m), 6.03 (1H, dd, J=9.6 Hz, 6.3 Hz), 3.72 (2H, s), 3.6–3.2 (10H, m), 2.6–2.5 (2H, m), 2.39 (4H, brs), 1.57 (4H, brs), 1.45 (2H, brs)

Elemental analysis: $C_{32}H_{39}N_5S_1 \cdot 1.0C_2H_2O_4 \cdot 0.5H_2O$

| | |
|---|---|
| Found (%) | C: 67.32, H: 6.52, N: 10.71 |
| Calculated (%) | C: 67.25, H: 6.41, N: 10.60 |

EXAMPLE 10

1-{2-(3-Piperidinomethylbenzylthio)ethyl}-3-(3-phenylpropyl)-2-imidazolidinylidenepropanedinitrile (Compound 10)

In dimethylformamide (DMF) (5 ml) was dissolved Compound (I) (276 mg) obtained in Reference Example 1, and potassium tert-butoxide (97 mg) was added thereto at 0° C., followed by stirring for 1.5 hours. Then, 18-crown-6 (229 mg) and 3-phenylbromopropane (220µl) were added to the mixture at room temperature, followed by stirring for 2 hours. An aqueous solution of sodium bicarbonate was added thereto, and the reaction mixture was extracted with chloroform. The extract was dried over potassium carbonate, and the solvent was evaporated under reduced pressure. The residue was purified by flash silica gel column chromatography (chloroform: methanol =100:1 to 20:1) to give Compound 10 (260 mg, 72%) as a colorless oily substance.

$^1$H NMR (270 MHz, CDCl$_3$) δ: 7.3–7.2 (9H, m), 3.75 (2H, s), 3.6–3.5 (10H, m), 2.73 (2H, t, J=6.9 Hz), 2.68 (2H, t, J=7.6 Hz), 2.36 (4H, brs), 1.98 (2H, tt, J=7.6 Hz, 7.6 Hz), 1.56 (4H, brs), 1.44 (2H, brs)

EXAMPLE 11

1-{2-(3-Piperidinomethylbenzylthio)ethyl}-3-{1-(8-methylnaphthyl)methyl}-2-imidazolidinylidenepropanedinitrile (Compound 11)

Compound 11 was prepared by following the procedure of Example 1, but replacing 1-naphthalenemethanol with 8-methylnaphthalenemethanol (44 mg). The resulting product was recrystallized in acetone in the form of an oxalate to give Compound 11 (110 mg, 81%) as colorless crystals.

$^1$H NMR (270 MHz, CDCl$_3$) δ: 7.82 (1H, d, J=7.9 Hz), 7.72 (1H, d, J=9.5 Hz), 7.4–7.2 (8H, m), 5.40 (2H, s), 3.79 (2H, s), 3.71 (2H, t, J=6.9 Hz), 3.6–3.2 (6H, m), 2.86 (3H, s), 2.80 (2H, t, J=6.9 Hz), 2.35 (4H, brs), 1.55 (4H, brs), 1.41 (2H, brs)

Elemental analysis: $C_{32}H_{35}N_5S_1 \cdot 1.0C_2H_2O_4 \cdot 0.1H_2O$

| | |
|---|---|
| Found (%) | C: 66.94, H: 6.55, N: 11.05 |
| Calculated (%) | C: 66.98, H: 6.30, N: 11.16 |

The chemical formulae of Compounds 1 to 11 are shown in Table 1.

TABLE 1

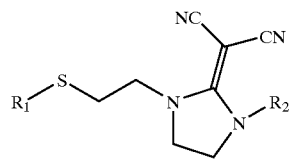

| Compound Number | R$_1$ | R$_2$ |
|---|---|---|
| 1 | | |

TABLE 1-continued
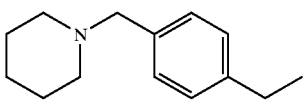
| Compound Number | R₁ | R₂ |
|---|---|---|
| 2 | 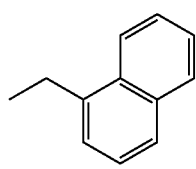 | 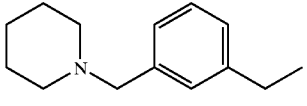 |
| 3 | 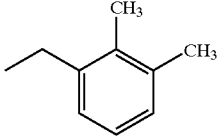 | 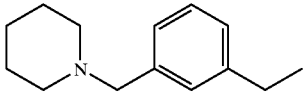 |
| 4 | 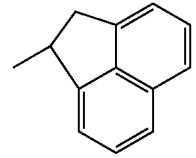 | 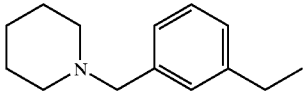 |
| 5 | 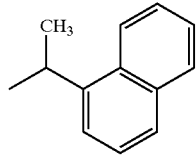 | 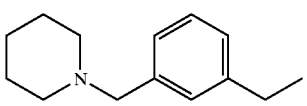 |
| 6 | 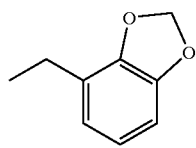 | 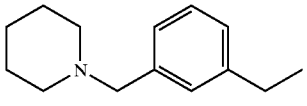 |
| 7 | 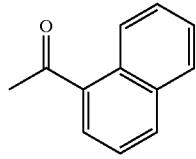 | 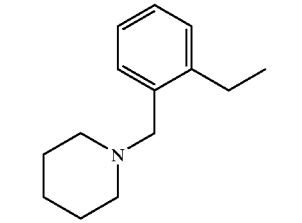 |
| 8 | 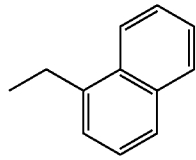 | |

TABLE 1-continued

| Compound Number | R₁ | R₂ |
|---|---|---|
| 9 | 3-piperidinomethylbenzyl | 1,2-diphenylpropyl (α-methylbibenzyl type) |
| 10 | 3-piperidinomethylbenzyl | 4-phenylbutyl |
| 11 | 3-piperidinomethylbenzyl | 1,8-dimethylnaphthalen-... (8-methyl, with ethyl) |

Reference Example 1

1-{2-(3-Piperidinomethylbenzylthio)ethyl}-2-imidazolidinylidenepropanedinitrile (Compound (I))

Step 1:

3-Piperidinomethylbenzylthiol (Compound (II))

In hydrochloric acid (150 ml) were dissolved 3-piperidinomethylbenzyl alcohol (7.1 g) and thiourea (2.9 g) at 0° C, and the solution was stirred at room temperature for 12 hours. The volume of hydrochloric acid was reduced under reduced pressure. A 4 mol/L aqueous solution of sodium hydroxide was added to the mixture, followed by stirring for 2 hours, and the mixture was extracted with diethyl ether. The extract was dried over potassium carbonate, and the solvent was evaporated to give Compound (II) as a pale yellow oily substance.

Step 2:

Bis(3-piperidinomethylbenzyl) disulfide (Compound (III))

In methanol was dissolved Compound (II) (8.3 g), and potassium carbonate was added thereto, followed by stirring at room temperature for about one day. Methylene chloride was added to the reaction mixture, followed by filtration. The solvent was evaporated to give Compound (III) (8.3 g) as a pale yellow oily substance.

Step 3:

1-{2-(3-Piperidinomethylbenzylthio)ethyl}-2-imidazolidinylidenepropanedinitrile (Compound (I))

In ethanol (50 ml) was dissolved Compound (III) (2.0 g), and sodium borohydride (385 mg) was added thereto. The mixture was heated under reflux for 45 minutes. After cooling to room temperature, 1-{(2-tosyloxy)ethyl}-2-imidazolidinylidenepropanedinitrile (2.8 g) was added thereto, followed by heating under reflux for 3 hours. The solvent was evaporated under reduced pressure, and an aqueous solution of sodium bicarbonate was added to the residue. The mixture was extracted with chloroform, and the extract was dried over potassium carbonate and subjected to silica gel column chromatography (chloroform: methanol= 100:1 to 10:1) to give Compound (I) (2.1 g, 65%) as pale yellow crystals.

$^1$H NMR (270 MHz, CDCl$_3$) δ: 7.3–7.2 (11H, m), 5.7 (1H, s), 3.8–3.5 (8H, m), 3.45 (2H, s), 2.76 (2H, t, J=6.7 Hz), 2.37 (4H, brs), 1.55 (4H, brs), 1.42 (2H), brs)

Reference Example 2

1-{2-(4-Piperidinomethylbenzylthio)ethyl}-2-imidazolidinylidenepropanedinitrile (Compound (IV))

Compound (IV) was obtained as colorless crystals as described in Reference Example 1.

hu 1H NMR (270 MHz, CDCl$_3$) δ: 7.27 (4H, s), 5.97 ($_1$H, brs), 3.76 (2H, s), 3.7–3.6 (6H, m), 3.44 (2H, s), 2.74 (2H, t, J=6.9 Hz), 2.36 (4H, brs), 1.56 (4H, brs), 1.42 (2H, brs)

Reference Example 3

1-{2-(2-Piperidinomethylbenzylthio)ethyl}-2-imidazolidinylidenepropanedinitrile (Compound (V))

Compound (V) was obtained as a pale yellow oily substance as described in Reference Example 1.

$^1$H NMR (270 MHz, CDCl$_3$) δ: 7.3–7.1 (4H, m), 3.8–3.6 (8H, m), 2.80 (2H, t, J=6.6 Hz), 2.36 (4H, brs), 1.53 (4H, brs), 1.43 (2H, brs)

Test Example
Preparation of CXCR3 Transfectants
Cells

L1/2 cells were grown in RPMI medium 1640, 10% Fetal Clone (Hyclone, Inc., Logan, Utah), 50 U/ml Penicillin/Streptomycin, 1 mmol/L NaPyruvate, and $5.5 \times 10^{-5}$ mol/L β-mercaptoethanol. Media components other than serum were purchased from GibcoBRL (Gaithersburg, Md). Two days prior to transfection, the L1/2 cells were diluted 1:5 into fresh medium. This resulted in 150 million cells in log phase growth at a concentration of about 1–3 million cells/ml.

CXCR3 DNA and Transfection

E. coli XL1 Blue cells (Stratagene, Inc., La Jolla, Calif.) were transformed with a pCDNA3-based (Invitrogen, San Diego, Calif.) CXCR3 cDNA expression plasmid (Qin, S. et al., J. Clin. Invest., 101: 746–754 (1998), Loetscher, M. et al., J. Exp. Med., 184: 963–969 (1996)) according to the manufacturer's protocol. Transformants were grown at 37° C. while shaking at 250 rpm in 500 ml of LB containing 100 μg/ml Ampicillin. The culture was then collected by centrifugation at 8,000 g, and the plasmid was purified using a Maxi plasmid purification column and protocol (Qiagen, Chatsworth, Calif.). Plasmid concentration and purity were determined using a 1% agarose gel and OD260/280 ratios. Plasmid DNA was suspended in ddH2O, and stored at −20° C. until use.

ScaI endonuclease was used to linearize the CXCR3 expression plasmid. 100 μg of DNA was digested with 10 μl of ScaI for 8 hours at 37° C. following the manufacturer's protocol (GibcoBRL, Cat# 15436–017). 20 μg was used directly in stable transfection (see below). 80 μg was cleaned of proteins and salts with a phenol: chloroform : isoamyl alcohol (25:24:1) extraction, 100% ethanol precipitation (with 0.1 volume $NH_4COOH$), and a 70% ethanol wash.

Stable transfectants of murine pre-B lymphoma cell line (L1/2) were prepared essentially as described (Ponath, P. D. et al., J. Exp. Med., 183: 2437–2448 (1996)). 25 million L1/2 cells in 0.8 ml of 1X PBS were electroporated with 20 μg of linearized DNA, 20 μg linearized DNA that had been cleaned (see above), or without DNA. Before electroporation, the L1/2 cells and the DNA were incubated for 10 minutes in 50 ml conical tubes (Falcon Model 2070, Becton Dickinson LabWare, Lincoln Park, N.J.) with gentle mixing (swirling) every 2 minutes. The L1.2 cell-DNA mixture was transferred into Gene Pulser cuvettes (BioRad, Richmond, Calif.) with a 0.4 cm electrode gap. The mixture was then electroporated at 250V and 960 μF, with the duration of shock and the actual voltage being measured. After electroporation, the cuvette was left undisturbed for 10 minutes at room temperature. All of the L1.2 cells-DNA mixture was then transferred to a T-25 tissue culture flask (Costar, Cambridge, Ma.), and grown for two days in 10 ml non-selective medium.

Selection

L1/2 cells expressing CXCR3 were then subjected to selection for neomycin resistance. After two days of growth in non-selective medium, 10 ml of 1.6 g/L G418 (GibcoBRL) was added to the culture for a final concentration of 0.8 g/L (the selective and maintenance concentration). This was then allowed to grow for 10 to 15 days, with fresh selective medium added when cells started to over-grow. Fresh selective medium consisted of RPMI-1640 supplemented with 10% bovine serum, 50 U/ml Penicillin/Streptomycin, 1 mmol/L NaPyruvate, $5.5 \times 10^{-5}$ mol/L β-mercaptoethanol and 0.8 g/L G418.

The cell surface expression of CXCR3 was assessed by chemotaxis. Ligand binding and Scatchard analysis were also used to monitor surface expression. After G418 selection, CXCR3 expressing L1/2 cells were selected based on chemotaxis ability. For each electroporation reaction culture, 30 ml (800,000 cells/ml) were collected, and suspended in 600 μl selective medium. Selective medium, 600 μl, containing 10 nmol/L IP-10, was placed into the bottom chamber of BioCoat cell culture plates from Becton Dickinson. 100 μl/well of the L1/2 cells were added to the top chamber of the BioCoat plates. The cells were then left to chemotax overnight in a $CO_2$ incubator at 37° C. The next day, the top chambers with the non-chemotaxing cells were removed. The cells which chemotaxed were collected from the bottom chamber, transferred into fresh medium and allowed to grow in a 24-well plate. They were subsequently expanded into a T-25 and then a T-75 flask from Costar.

Transfectants expressing high level of receptors were cloned by limiting dilution. CXCR3 transfected cells were diluted to between 30 cells/ml and 3 cell/ml in selection medium containing G418. Aliquots of the dilutions were added to 96-well tissue culture plates at 100 μl/well. After 14 days at 37° C. and 5% $CO_2$, wells containing single colonies were identified under an inverted microscope. 50 μl of the cells were then transferred and stained with anti-CXCR3 mAb and analyzed by flow cytometry as described (Qin, S. et al., J. Clin. Invest., 101: 746–754 (1998)). The level of receptor expression correlated with mean fluorescence intensity and cells which expressed high levels of CXCR3 were selected. Once a stable cell line was established, the line was expanded for use, and is referred to herein as CXCR3.L1/2.

CXCR3/IP-10 Radioligand Binding
CXCR3.L1/2 Membrane Preparation

CXCR3.L1/2 cells were pelleted by centrifugation and stored at −80° C.. The cells were lysed by thawing and resuspending at about $1.5 \times 10^7$ cells/ml in a hypotonic buffer (5 mmol/L HEPES (pH 7.2), 2 mmol/L EDTA, 10 μg/ml each leupeptin, aprotinin, and chymostatin, and 100 μg/ml PMSF (all from Sigma, St. Louis)). Nuclei and cellular debris was removed by centrifugation (500 g to 100 g, at 4° C.) for 10 min. The supernatant was transferred to chilled centrifuge tubes (Nalge, Rochester, N.Y.) and the membrane fraction was recovered by centrifugation (25,000 g at 4° C.) for 45 min. The membrane pellet was resuspended in freezing buffer (10 mM HEPES (pH 7.2), 300 mmol/L Sucrose, 5 μg/ml each of leupeptin, aprotinin, and chymostatin, and 10 μg/ml PMSF). The total protein concentration was determined using a coomassie blue staining protein concentration assay kit (BioRad). The membrane preparation was aliquoted and stored at −80° C. until time of use.

Binding Assay

CXCR3/IP-10 binding was performed in 96-well polypropylene plates (Costar) in a final volume of 0.1 ml of HBB buffer (50 mmol/L Hepes pH 7.4, 1 mmol/L $CaCl_2$, 5 mmol/L $MgCl_2$, 0.02% sodium azide, 0.5% BSA (bovine serum albumin)) containing 1 to 5 μg of CXCR3.L1/2 transfectant cell membrane protein and 0.05 to 0.2 nmol/L $^{125}$I-labeled IP-10 (NEN, Boston, Mass.). Competition binding experiments were performed by including variable concentrations of unlabeled IP-10 or test compound. Nonspecific binding was determined following the addition of a 250 nmol/L unlabelled IP-10. Samples were incubated for 60 min at room temperature, and bound and free tracer ($^{125}$I-IP10) were separated by filtration through 96-well GF/B filterplates (Packard) presoaked in 0.3% polyethyleneimine. The filters were washed in HBB further supplemented with 0.5 mol/L NaCl, dried, and the amount of bound radioactivity determined by liquid scintillation counting. The competition is presented as the percent specific binding as calculated by 100×[(S−B)/(T−B)], where S is the radioactivity bound for each sample, B is background binding, and T is total bound in the absence of competitors. Duplicates were used throughout the experiments. The results are shown in Table 2.

TABLE 2

| Compound Number | % inhibition at 10 μmol/L |
|---|---|
| 1 | 108 |
| 2 | 94 |
| 3 | 91 |
| 4 | 95 |
| 6 | 84 |
| 7 | 93 |
| 10 | 86 |
| 11 | 96 |

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An imidazolidine compound having the structural formula:

$$R^{11a}R^{11b}N-(CH_2)_m-W-\underset{R^8\ R^7}{\underset{|}{\overset{R^9\ R^{10}}{\overset{|}{\diagdown}}}}\underset{R^{6b}}{\overset{R^{6a}}{\overset{|}{-C-}}}S-\left(\underset{R^{5b}}{\overset{R^{5a}}{\overset{|}{-C-}}}\right)_n\underset{R^{4b}}{\overset{R^{4a}}{\overset{|}{-C-}}}N\underset{R^{3b}\ R^{3a}(CH_2)_p\ R^{2b}}{\underset{|}{\overset{|}{-}}}\overset{X^1\diagdown\diagup X^2}{\overset{C}{\overset{\|}{-}}}N-Y-R^1 \quad (I)$$

or physiologically acceptable salt thereof, wherein:
W is
  a bond,
  —O—,
  —S—, or
  —NR$^{12}$—, wherein
  R$^{12}$ is
    hydrogen,
    substituted or unsubstituted lower alkyl,
    substituted or unsubstituted cycloalkyl,
    substituted or unsubstituted aryl,
    substituted or unsubstituted aralkyl, or
    substituted or unsubstituted heteroarylalkyl;
X$^1$ and X$^2$ are each, independently,
  hydrogen,
  —CN,
  —NO$_2$,
  —SO$_2$R$^{13a}$,
  —SO$_2$NR$^{13a}$R$^{13b}$,
  —C(=O)—R$^{13a}$,
  —C(=O)—OR$^{13a}$, or
  —C(=O)—NR$^{13a}$R$^{13b}$, wherein
  R$^{13a}$ and R$^{13b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
Y is
  a bond,
  —(C=O)—, or
  —(CR$^{14a}$R$^{14}$)—, wherein
  R$^{14a}$ and R$^{14b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
R$^1$ is
  substituted or unsubstituted lower alkyl,
  substituted or unsubstituted cycloalkyl,
  substituted or unsubstituted polycycloalkyl,
  substituted or unsubstituted lower alkenyl,
  substituted or unsubstituted cycloalkenyl,
  substituted or unsubstituted aryl,
  substituted or unsubstituted heteroaryl,
  substituted or unsubstituted aralkyl, or
  substituted or unsubstituted heteroarylalkyl;
R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each, independently,
  hydrogen,
  substituted or unsubstituted lower alkyl,
  substituted or unsubstituted cycloalkyl,
  substituted or unsubstituted aryl,
  substituted or unsubstituted aralkyl, or
  substituted or unsubstituted heteroarylalkyl;
R$^7$, R$^8$, R$^9$ and R$^{10}$ are each, independently,
  hydrogen,
  hydroxy,
  substituted or unsubstituted lower alkyl,
  substituted or unsubstituted lower alkoxy,
  substituted or unsubstituted lower alkanoyl,
  substituted or unsubstituted lower alkanoyloxy
  substituted or unsubstituted lower alkoxycarbonyl,
  substituted or unsubstituted aryl,
  substituted or unsubstituted heteroaryl,
  halogen,
  —CN,
  —NO$_2$,
  —COOR$^{15a}$,
  —NR$^{15a}$R$^{15b}$, or
  —CONR$^{15a}$R$^{15b}$, wherein
  R$^{5a}$ and R$^{15b}$ are each, independently,
    hydrogen,
    substituted or unsubstituted lower alkyl,
    substituted or unsubstituted cycloalkyl,
    substituted or unsubstituted aryl, or
    substituted or unsubstituted aralkyl, or
  R$^{15a}$ and R$^{15b}$ taken together with the nitrogen atom to which they are bonded a substituted or unsubstituted heterocyclic group containing at least one nitrogen atom;
R$^{11a}$ and R$^{11b}$ are each, independently,
  hydrogen,
  substituted or unsubstituted lower alkyl,
  substituted or unsubstituted cycloalkyl,
  substituted or unsubstituted aryl, or
  substituted or unsubstituted aralkyl, or
R$^{11a}$ and R$^{11b}$ taken together with the nitrogen atom to which they are bonded form a substituted or unsubstituted heterocyclic group containing at least one nitrogen atom;
n is an integer form zero to about 4;
n is an integer form zero to about 6; and p is an integer form zero to about 2.

2. The imidazolidine compound according to claim 1, wherein $R^1$ is substituted or unsubstituted aryl, substituted or unsubstituted heteroaryl, substituted or unsubstituted aralkyl, or substituted or unsubstituted heteroarylalkyl.

3. The imidazolidine compound according to claim 1, wherein $X^1$ and $X^2$ are each —CN.

4. The imidazolidine compound according to claim 1, wherein W is a bond or —O—.

5. The imidazolidine compound according to claim 1, wherein W is at the para- or meta-position of the benzene ring from the —$CR^{6a}R^{6b}$— group.

6. The imidazolidine compound according to claim 1, wherein $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^7$, $R^8$, $R^9$, and $R^{10}$ are hydrogen.

7. The imidazolidine compound according to claim 1, wherein
   $R^{11a}$ and $R^{11b}$ are each, independently hydrogen or a substituted or unsubstituted lower alkyl, or
   $R^{11a}$ and $R^{11b}$ taken together with the nitrogen atom to which they are bonded form a substituted or unsubstituted heterocyclic ring containing at least one nitrogen atom.

8. The imidazolidine compound according to claim 1, wherein
   W is a bond or —O—;
   $X^1$ and $X^2$ are each —CN;
   $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^7$, $R^8$, $R^9$, and $R^{10}$ are hydrogen;
   p is 0; and
   n is 1.

9. The imidazolidine compound according to claim 8, wherein W is at the para- or meta-position of the benzene ring from the —$CR^{6a}R^{6b}$— group.

10. The imidazolidine compound according to claim 9, wherein $R^1$ is substituted or unsubstituted aryl, substituted or unsubstituted heteroaryl, substituted or unsubstituted aralkyl, or substituted or unsubstituted heteroarylalkyl.

11. The imidazolidine compound according to claim 10, wherein
    $R^{11a}$ and $R^{11b}$ are each, independently hydrogen or a substituted or unsubstituted lower alkyl, or
    $R^{11a}$ and $R^{11b}$ taken together with the nitrogen atom to which they are bonded form a substituted or unsubstituted heterocyclic ring containing at least one nitrogen atom.

12. A composition comprising the imidazolidine compound according to claim 1 and a physiologically acceptable carrier.

13. A method of inhibiting inflammation in an individual, comprising administering to the individual a therapeutically effective amount of an imidazolidine compound having the structural formula:

(I)

[chemical structure]

or physiologically acceptable salt thereof, wherein:
W is
    a bond,
    —O—,
    —S—, or
    —NR$^{12}$—, wherein
        $R^{12}$ is
            hydrogen,
            substituted or unsubstituted lower alkyl,
            substituted or unsubstituted cycloalkyl,
            substituted or unsubstituted aryl,
            substituted or unsubstituted aralkyl, or
            substituted or unsubstituted heteroarylalkyl;
$X^1$ and $X^2$ are each, independently,
    hydrogen,
    —CN,
    —NO$_2$,
    —SO$_2$R$^{13a}$,
    SO$_2$NR$^{13a}$R$^{13b}$,
    —C(=O)—R$^{13a}$,
    C(=O)—OR$^{13a}$, or
    —C(=O)—NR$^{13a}$R$^{13b}$, wherein
        $R^{13a}$ and $R^{3b}$ are each, independently,
            hydrogen,
            substituted or unsubstituted lower alkyl,
            substituted or unsubstituted cycloalkyl,
            substituted or unsubstituted aryl, or
            substituted or unsubstituted aralkyl;
Y is
    a bond,
    —(C=O)—, or
    —(CR$^{14a}$R$^{14b}$)—, wherein
        $R^{14a}$ and $R^{14b}$ are each, independently,
            hydrogen,
            substituted or unsubstituted lower alkyl,
            substituted or unsubstituted cycloalkyl,
            substituted or unsubstituted aryl, or
            substituted or unsubstituted aralkyl;
$R^1$ is
    substituted or unsubstituted lower alkyl,
    substituted or unsubstituted cycloalkyl,
    substituted or unsubstituted polycycloalkyl,
    substituted or unsubstituted lower alkenyl,
    substituted or unsubstituted cycloalkenyl,
    substituted or unsubstituted aryl,
    substituted or unsubstituted heteroaryl,
    substituted or unsubstituted aralkyl, or
    substituted or unsubstituted heteroarylalkyl;
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently,
    hydrogen,
    substituted or unsubstituted lower alkyl,
    substituted or unsubstituted cycloalkyl,
    substituted or unsubstituted aryl,
    substituted or unsubstituted aralkyl, or
    substituted or unsubstituted heteroarylalkyl;
$R^7$, $R^8$, $R^9$ and $R^{10}$ are each, independently,
    hydrogen,
    hydroxy,
    substituted or unsubstituted lower alkyl,
    substituted or unsubstituted lower alkoxy,
    substituted or unsubstituted lower alkanoyl,
    substituted or unsubstituted lower alkanoyloxy
    substituted or unsubstituted lower alkoxycarbonyl ,
    substituted or unsubstituted aryl,
    substituted or unsubstituted heteroaryl,
    halogen,
    —CN, —NO₂,
—COOR¹⁵ᵃ,
—NR¹⁵ᵃR¹⁵ᵇ, or
—CONR¹⁵ᵃR¹⁵ᵇ, wherein
  R¹⁵ᵃ and R¹⁵ᵇ are each, independently,
  hydrogen,
  substituted or unsubstituted lower alkyl,
  substituted or unsubstituted cycloalkyl,
  substituted or unsubstituted aryl,
  substituted or unsubstituted aralkyl, or
  R¹⁵ᵃ and R¹⁵ᵇ taken together with the nitrogen atom to which they are bonded a substituted or unsubstituted heterocyclic group containing at least one nitrogen atom;
R¹¹ᵃ and R¹¹ᵇ are each, independently,
  hydrogen,
  substituted or unsubstituted lower alkyl,
  substituted or unsubstituted cycloalkyl,
  substituted or unsubstituted aryl,
  substituted or unsubstituted aralkyl, or
  R¹¹ᵃ and R¹¹ᵇ taken together with the nitrogen atom to which they are bonded form a substituted or unsubstituted heterocyclic group containing at least one nitrogen atom;
n is an integer form zero to about 4;
m is an integer form zero to about 6; and
p is an integer form zero to about 2.

14. The method of claim 13, wherein said inflammation is a consequence of an autoimmune disease.

15. The method of claim 13, wherein said inflammation is a consequence of an allergic disease or condition.

16. The method of claim 13, wherein said inflammation is a consequence of infection.

17. The method of claim 16, wherein said infection is bacterial, viral, fungal or parasitic.

18. A method of treating an individual having a disease associated with pathogenic leukocyte recruitment and/or activation, comprising administering to the individual a therapeutically effective amount of an imidazolidine compound having the structural formula (I):

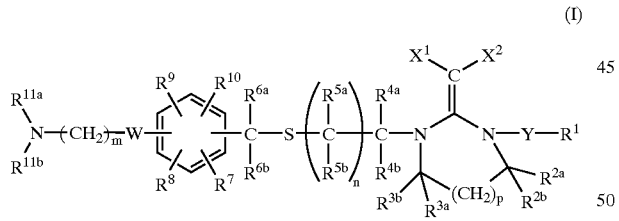

(I)

or physiologically acceptable salt thereof, wherein:
W is
  a bond,
  —O—,
  —S—, or
  —NR¹²—, wherein
    R¹² is
      hydrogen,
      substituted or unsubstituted lower alkyl,
      substituted or unsubstituted cycloalkyl,
      substituted or unsubstituted aryl,
      substituted or unsubstituted aralkyl, or
      substituted or unsubstituted heteroarylalkyl;
X¹ and X²⁻ are each, independently,
  hydrogen,
  —CN,
  —NO₂,
  —SO₂R¹³ᵃ,
  —SO₂NR¹³ᵃR¹³ᵇ,
  —C(=O)—R¹³ᵃ,
  —C(=O)—OR¹³ᵃ or
  —C(=O)—NR¹³ᵃR¹³ᵇ, wherein
    R¹³ᵃ and R¹³ᵇ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
Y is
  a bond,
  —(C=O)—, or
  —(CR¹⁴ᵃR¹⁴ᵇ)—, wherein
    R¹⁴ᵃ and R¹⁴ᵇ are each, independently,
    hydrogen,
    substituted or unsubstituted lower alkyl,
    substituted or unsubstituted cycloalkyl,
    substituted or unsubstituted aryl, or
    substituted or unsubstituted aralkyl;
R¹ is
  substituted or unsubstituted lower alkyl,
  substituted or unsubstituted cycloalkyl,
  substituted or unsubstituted polycycloalkyl,
  substituted or unsubstituted lower alkenyl,
  substituted or unsubstituted cycloalkenyl,
  substituted or unsubstituted aryl,
  substituted or unsubstituted heteroaryl,
  substituted or unsubstituted aralkyl, or
  substituted or unsubstituted heteroarylalkyl ;
R²ᵃ, R²ᵇ, R³ᵃ, R³ᵇ, R⁴ᵃ, R⁴ᵇ, R⁵ᵃ, R⁵ᵇ, R⁶ᵃ, and R⁶ᵇ are each, independently,
  hydrogen,
  substituted or unsubstituted lower alkyl,
  substituted or unsubstituted cycloalkyl,
  substituted or unsubstituted aryl,
  substituted or unsubstituted aralkyl, or
  substituted or unsubstituted heteroarylalkyl;
R⁷, R⁸, R⁹ and R¹⁰ are each, independently,
  hydrogen,
  hydroxy,
  substituted or unsubstituted lower alkyl,
  substituted or unsubstituted lower alkoxy,
  substituted or unsubstituted lower alkanoyl,
  substituted or unsubstituted lower alkanoyloxy
  substituted or unsubstituted lower alkoxycarbonyl,
  substituted or unsubstituted aryl,
  substituted or unsubstituted heteroaryl,
  halogen,
  —CN,
  —NO₂,
  —COOR¹⁵ᵃ,
  —NR¹⁵ᵃR¹⁵ᵇ, or
  —CONR¹⁵ᵃR¹⁵ᵇ, wherein
    R¹⁵ᵃ and R¹⁵ᵇ are each, independently,
    hydrogen,
    substituted or unsubstituted lower alkyl,
    substituted or unsubstituted cycloalkyl,
    substituted or unsubstituted aryl, or
    substituted or unsubstituted aralkyl, or
    R¹⁵ᵃ and R¹⁵ᵇ taken together with the nitrogen atom to which they are bonded a substituted or unsubstituted heterocyclic group containing at least one nitrogen atom;

$R^{11a}$ and $R^{11b}$ are each, independently,
  hydrogen,
  substituted or unsubstituted lower alkyl,
  substituted or unsubstituted cycloalkyl,
  substituted or unsubstituted aryl, or
  substituted or unsubstituted aralkyl, or
$R^{11a}$ and $R^{11b}$ taken together with the nitrogen atom to which they are bonded form a substituted or unsubstituted heterocyclic group containing at least one nitrogen atom;
n is an integer form zero to about 4;
m is an integer form zero to about 6; and
p is an integer form zero to about 2.

19. The method of claim 18, wherein said disease is an autoimmune disease.

20. The method of claim 18, wherein said disease is an allergic disease or condition.

21. The method of claim 18, wherein said disease is graft rejection.

* * * * *

UNITED STATES PATENT AND TRADEMARK OFFICE
CERTIFICATE OF CORRECTION

PATENT NO.    : 6,495,569 B1
DATED         : December 17, 2003
INVENTOR(S)   : Etsuo Ohshima et al.

It is certified that error appears in the above-identified patent and that said Letters Patent is hereby corrected as shown below:

<u>Column 28,</u>
Line 4, delete "- $(CR^{14a}R^{14})$ -" and insert -- - $(CR^{14a}R^{14b})$ - --.
Line 46, delete "$R^{5a}$" and insert -- $R^{15a}$ --.

<u>Column 30,</u>
Line 4, delete "-$NR^2$-" and insert -- -$NR^{12}$- --.

Signed and Sealed this

Tenth Day of June, 2003

JAMES E. ROGAN
*Director of the United States Patent and Trademark Office*